(12) United States Patent
Butler et al.

(10) Patent No.: US 7,536,266 B2
(45) Date of Patent: May 19, 2009

(54) UNIVERSAL X-RAY FLUORESCENCE CALIBRATION TECHNIQUE FOR WIRE SURFACE ANALYSIS

(75) Inventors: Kevin Butler, Broadview Heights, OH (US); Patrick R. Brennan, Concord, OH (US)

(73) Assignee: Lincoln Global, Inc., Santa Fe Springs, CA (US)

( * ) Notice: Subject to any disclaimer, the term of this patent is extended or adjusted under 35 U.S.C. 154(b) by 473 days.

(21) Appl. No.: 11/405,165

(22) Filed: Apr. 17, 2006

(65) Prior Publication Data

US 2008/0061223 A1  Mar. 13, 2008

(51) Int. Cl.
G01D 18/00 (2006.01)
G06F 17/40 (2006.01)

(52) U.S. Cl. ............... 702/85; 702/104; 250/252.1; 250/339.09

(58) Field of Classification Search ........... 702/85, 702/30, 32, 121
See application file for complete search history.

(56) References Cited

U.S. PATENT DOCUMENTS

| | | | |
|---|---|---|---|
| 5,225,661 A | 7/1993 | Chai et al. | |
| 5,939,718 A | 8/1999 | Yamada et al. | |
| 6,002,129 A | 12/1999 | Ito et al. | |
| 6,041,096 A | 3/2000 | Doi et al. | |
| 6,146,768 A | 11/2000 | Masaie et al. | |
| 6,265,717 B1 | 7/2001 | Sakata et al. | |
| 6,569,383 B1 | 5/2003 | Nelson et al. | |
| 6,615,151 B1* | 9/2003 | Sceccina et al. | 702/85 |
| 6,841,246 B2 | 1/2005 | Shimizu et al. | |
| 6,864,978 B1* | 3/2005 | Hazen et al. | 356/326 |
| 6,882,701 B2 | 4/2005 | Ferrandino et al. | |
| 6,887,713 B2 | 5/2005 | Nelson et al. | |
| 6,906,285 B2 | 6/2005 | Zucker et al. | |
| 6,937,691 B2 | 8/2005 | Yamagami et al. | |
| 7,098,037 B2* | 8/2006 | Haas et al. | 436/95 |
| 2003/0154044 A1* | 8/2003 | Lundstedt et al. | 702/104 |
| 2005/0036583 A1 | 2/2005 | Chen et al. | |
| 2005/0109936 A1 | 5/2005 | Yun et al. | |
| 2007/0112258 A1* | 5/2007 | Soyemi et al. | 600/310 |

OTHER PUBLICATIONS

PerkinElmerSCIEX Instruments, "ICP Mass Spectrometry, The 30-Minute Guide to ICP-MS", 2001 PerkinElmer, Inc., 8 pgs.

* cited by examiner

*Primary Examiner*—Hal D Wachsman
(74) *Attorney, Agent, or Firm*—Hahn Loeser & Parks LLP; Keith J. Marcinowski

(57) ABSTRACT

A non-flat sample is analyzed by a first spectrometer which has previously been calibrated for flat sample analysis. The non-flat sample is then analyzed by a second spectrometer calibrated for flat samples. The values collected from analysis of the non-flat sample by the first spectrometer are plotted against values collected from analysis of non-flat samples by the second spectrometer. The plot identifies a differences between the first spectrometer values and the second spectrometer values. The plot values are used in conjunction with the standard values from the first spectrometer to calculate final standard values for the second spectrometer. Final standard values for the second spectrometer are then used to generate calibration curves for the second spectrometer.

20 Claims, 6 Drawing Sheets

UNIVERSAL X-RAY FLUORESCENCE CALIBRATION TECHNIQUE FOR WIRE SURFACE ANALYSIS

BACKGROUND

The present application relates to analytical instruments, and more particularly to methods and techniques for calibrating analytical instruments to permit their use for analyzing materials having non-flat, repeating surface patterns. The application is particularly suited to fluorescence measurement of non-flat surfaces with repeating patterns such as welding wire, but may also be implemented for other appropriate applications.

One particular fluorescence technique known as X-ray fluorescence analysis is used to identify elements and the concentration of elements, which comprise a material under investigation. This and similar techniques involve irradiating an area with a high energy beam, such as X-rays, gamma rays, neutrons or particle beams and observing the resulting fluorescence emitted by the irradiated area.

Such systems generally include a source of excitation radiation, an optic for directing the radiation toward a sample, a radiation detector to detect the stimulated fluorescence emissions from the sample (possibly through another optic), and a display for displaying the spectral output.

In X-ray fluorescence spectroscopy, for example, as the excitation photons strike the sample, they knock electrons out of their orbits around the nuclei of the atoms in the sample, creating vacancies that destabilize the atoms. The atoms stabilize when electrons from the outer orbits are transferred to the inner orbits. These atoms emit a characteristic X-ray fluorescence photon representing the difference between the two binding energies of the corresponding orbits. The detector collects this spectrum of photons and converts them to electrical impulses proportional to the energies of the various X-rays in the sample's spectrum. Since each element has a different and identifiable X-ray fluorescence signature, an operator can determine the presence and concentration of the element(s) within the sample by reviewing specific areas of the emitted spectrum.

While X-ray fluorescence spectroscopy has been employed as a tool in many industries where rapid, repeatable elemental measurements of materials are useful, the state of the current technology does not sufficiently support the capability of analyzing non-flat surfaces. Rather, existing analysis techniques require the surface of the sample presented to the spectrometer have a flat surface in order to perform highly accurate analysis. This becomes a particular limitation in those industries where the materials to be analyzed do not commonly have a flat surface, or where it is quite difficult to modify the sample to yield a flat area for analysis. One particular situation where such measurements become difficult is in the measurement of rods, wires or electrodes used in the welding industry.

This problem is compounded when an organization employs multiple analytical devices. In view of these issues, it would be beneficial to calibrate analytical devices to accurately measure non-flat samples, and to achieve consistent readings of non-flat samples among multiple analytical devices.

Therefore, it is considered useful to provide an improved calibration technique and system which permits for the calibration of analytical instruments, such as spectrometers, for analysis of samples having non-flat repeating surfaces, and to extend the calibration technique to multiple analytical instruments of the same type. It would also be useful for the technique to be designed for use where a user does not need to know the actual concentration of elements of a sample material, to produce materials having appropriate characteristics.

BRIEF DESCRIPTION

A method and system is provided for calibrating a plurality of analytical devices for analysis of non-flat surfaces. Initially, a non-flat sample is analyzed by a first analytical device which has previously been calibrated for flat sample analysis. The standard values for use in flat sample analysis have therefore previously been generated. Values generated by the analysis of the non-flat sample undertaken by the first spectrometer are collected. A non-flat sample is then analyzed by a second spectrometer where the second spectrometer has also been calibrated for flat samples. Value generated by analysis of the non-flat sample undertaken by the second spectrometer are then collected. The values collected from the analysis of the non-flat sample by the first spectrometer are plotted against the values collected from the analysis of the non-flat samples by the second spectrometer. The plot identifies differences between the first spectrometer values and the second spectrometer values. The plot values are used in conjunction with the standard values from the first spectrometer to calculate final standard values for the second spectrometer. Final standard values for the second spectrometer are then used to generate calibration curves for the second spectrometer.

DETAILED DESCRIPTION

Figure 1:
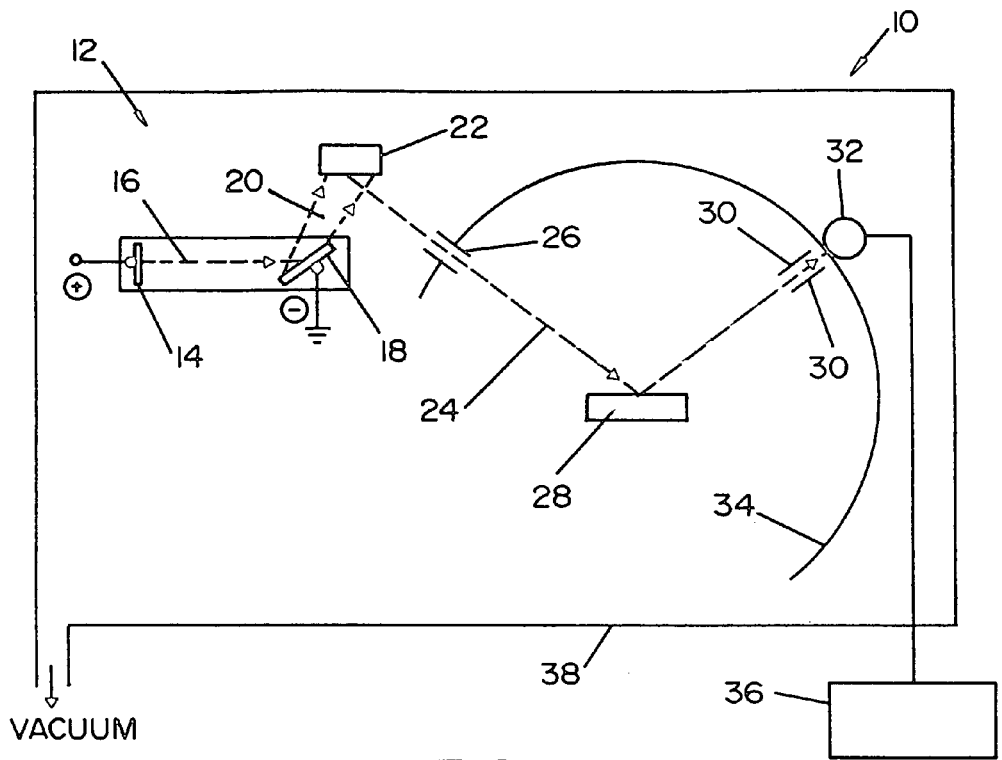
FIG. 1 is a schematic diagram of components of a typical wave length-dispersive X-ray fluorescence spectrometer system.

FIG. 1 provides a schematic diagram of an analytical device 10, such as an X-ray fluorescence (XRF) spectrometer or other similar device used to analyze a material sample for its constituent elements and concentrations of the elements. This simplified figure shows beam generator 12, such as an X-ray tube which consists of a cathode 14 running a current of approximately 40-60 milliamps (mA) producing electrons 16 that are accelerated by a voltage of approximately 5 to 100 keV and fired at a target anode 18, which generates broadband continuum X-rays 20. The resulting X-rays 20 are directed to a sample 22, causing emission of X-rays 24 which are characteristic of constituent elements of sample 22. The emitted characteristic X-rays 24 are collimated by a collimator 26 and diffracted by an analyzing crystal 28 and again collimated by a collimator 30. The X-rays 24 intensities are measured using detector 32 mounted on a goniometer 34. The output of detector 32 is then manipulated and displayed on display 36, commonly as a spectrum of the sample. Components of analytical device 10 may be located in a vacuum 38 to avoid oxidation and to minimize absorption of the X-rays by air.

It is to be appreciated that the above description is a generalized depiction of a particular analytical device, and other configurations may also be used in accordance with the present application. Particularly, it is to be understood that the concepts of the present application may also be used in other laser or beam based systems implemented for detection and analysis. Additionally, the following discussion related to the calibration of an analytical device is applicable to the calibration of multiple analytical devices, and therefore the analytical device of FIG. 1 is intended to represent multiple analytical devices which may be used in accordance with the present concepts.

Figure 2:
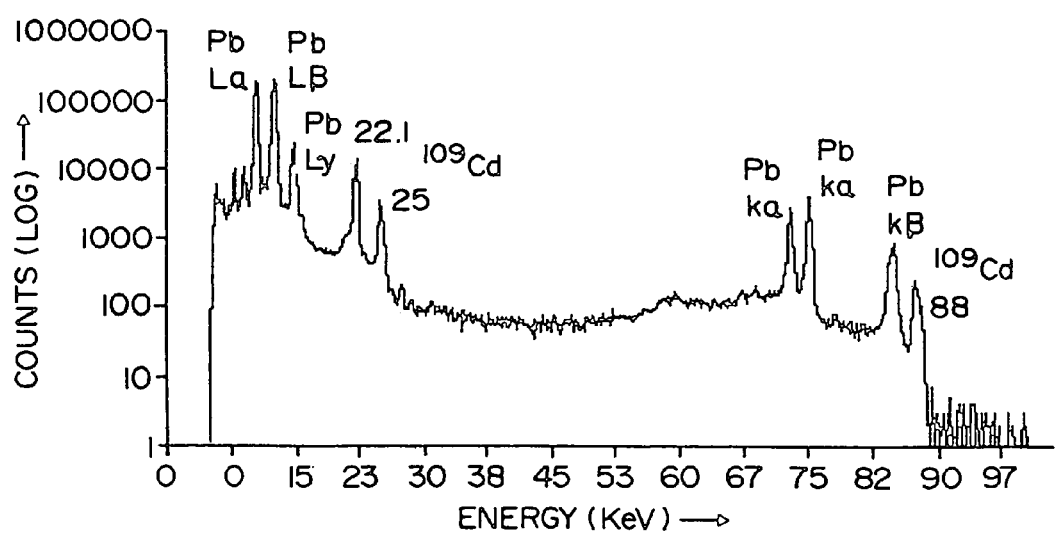
FIG. 2 is an exemplary spectrum with energy (keV) versus counts (log), generated by an X-ray fluorescence device.

Turning to FIG. 2, shown is a representative spectrum output which may be obtained and displayed on display 36 by the operation of device 10 of FIG. 1. As depicted, the spectral peaks represent characteristic elements and quantities of the elements of a particular sample, where the spectrum plots energy levels (keV) versus quantities of such element (Counts).

The value of the output generated by an analytical device, is dependent on the accuracy of the device. In an ideal situation, two different analytical devices would return the same raw intensities for the same material sample. However, each analytical device may have slightly different characteristics. For example, the detectors may not be identical, or positioning of the components within the device, resulting in dissimilar outputs. This is true even if the devices are from the same company and of the same model type. Therefore, it is desirable to calibrate these devices against a sample or specimen having known characteristics. For example, a specimen or sample may be certified by a certification association as having a certain type and percentage of elements. Alternatively, an organization may maintain their own master samples having known characteristics.

Figure 3A:
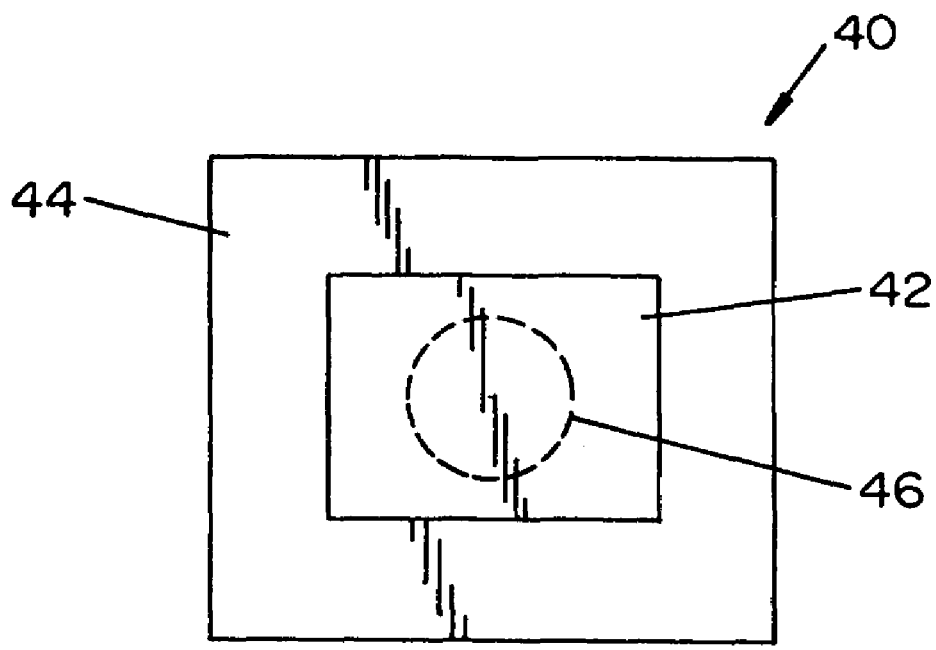
FIGS. 3A-3B represent a flat specimen or sample used in calibrating an analytical device such as an X-ray fluorescence spectrometer.
Figure 3B:
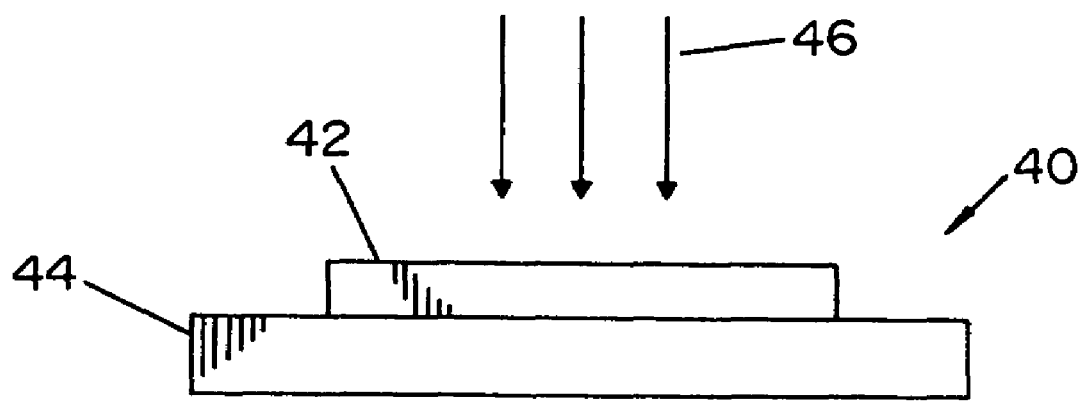

An exemplary sample or specimen arrangement 40 is shown in FIGS. 3A-3B. Particularly, a sample 42 is held on a carrier 44, and is depicted as having a flat upper surface which will receive the beam from the analytical device. Carrier 44 may be any appropriate carrier used to hold sample 42, such as a holder made of PTFE. A sample with a flat surface will result in consistent reflection of an incident beam onto and from the sample. For example, analysis beam window 46 will impinge and reflect from the surface of sample 42 in a uniform manner. On the other hand, a non-flat sample will result in less consistent and predictable beam reflection.

Calibrating an analytical device, such as a spectrometer, for samples with flat surfaces can be accomplished by a number of known processes. One such process is illustrated by the flow diagram of FIG. 4. In step 50, a sample having a flat or planar surface is located within a detection area of an analytical device. The sample has known material characteristics which have been certified by a certification agency or otherwise determined and may be called a master sample. One particular material which may be used as a master sample is glass comprised of known elements and concentrations. Also, while the above mentions a single master sample, it is to be understood that more than one master sample may be used in the calibration procedure. Particularly, the process of FIG. 4 may be repeated for a plurality of master samples to obtain a range of elements and or concentrations.

Once, as in step 52, the sample has been appropriately positioned with reference to the analytical device, it is analyzed by the analytical device. The results of the analysis are compared to the known material characteristics, in step 54. Based on the comparison operation of step 54, a determination is made, in step 56, as to the differences between the known characteristics of the sample and the results obtained by the analysis in step 54. Using these determined differences, step 58 then calibrates the analytical device.

Figure 5:
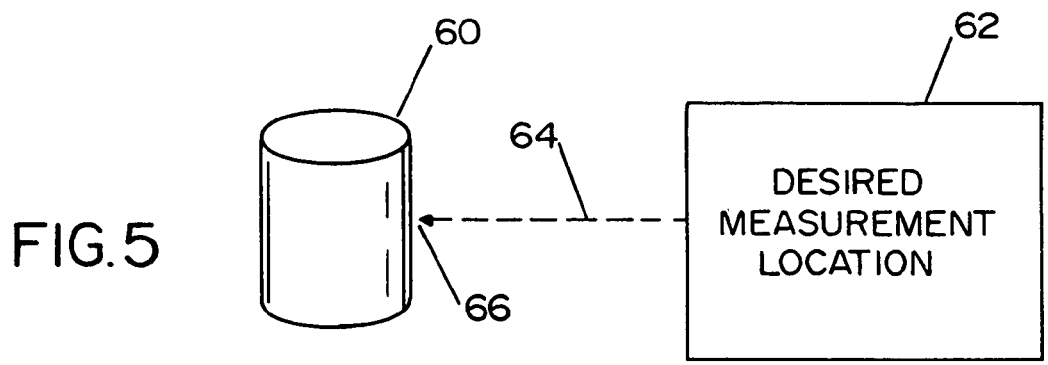
FIG. 5 illustrates a radial measurement of a rod, wire or electrode.

This or other techniques for calibrating an analytical device for flat surface samples, may be undertaken for a number of analytical devices. Once the devices have each been calibrated, if another sample is then analyzed, each of the devices will output substantially the same readings. However, even if these analytical devices have been calibrated for flat surface samples, and if each of the devices then analyze the same sample with non-flat surface, consistent readings among the devices will not occur due to the surface variations. This concept is illustrated in FIG. 5, where sample 60 may be a wire, rod or electrode used in the welding industry and is positioned in relationship to beam generator 62, such that emitted beams 64 will impinge on the surface of sample 60. However, as is illustrated, the desired measurement location 66 is necessarily on a curved portion of the surface of sample 60 which results in unpredictable reflection and absorption rates.

Presently, in order to accurately analyze non-flat surface samples, a technique such as Fourier Transform Infra-Red (FTIR) spectroscopy technique needs to be used. However, this technique requires movement of the investigative beam across the non-planar surface and highly complex reconstruction algorithms.

Figure 6A:
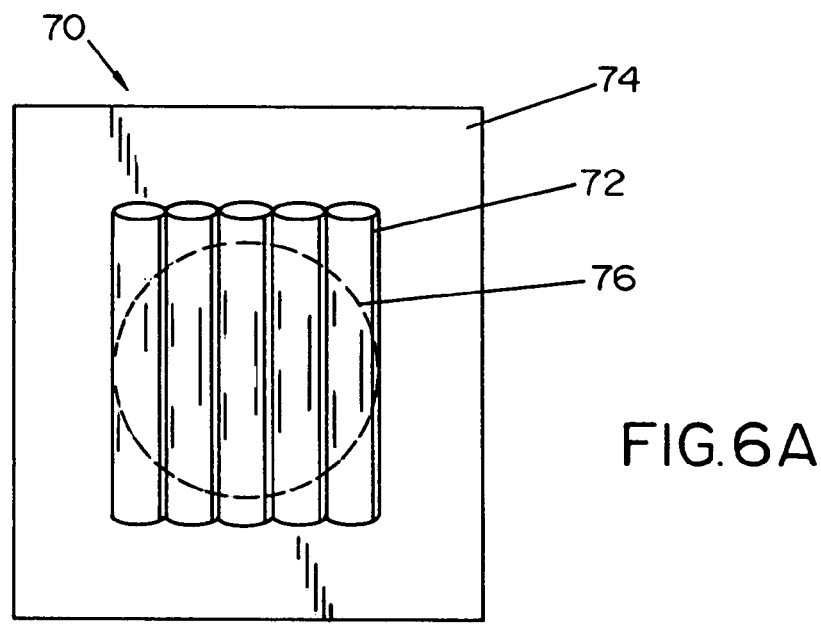
FIGS. 6A-6B illustrates a non-flat specimen or sample used for the calibration technique of the present application.
Figure 6B:
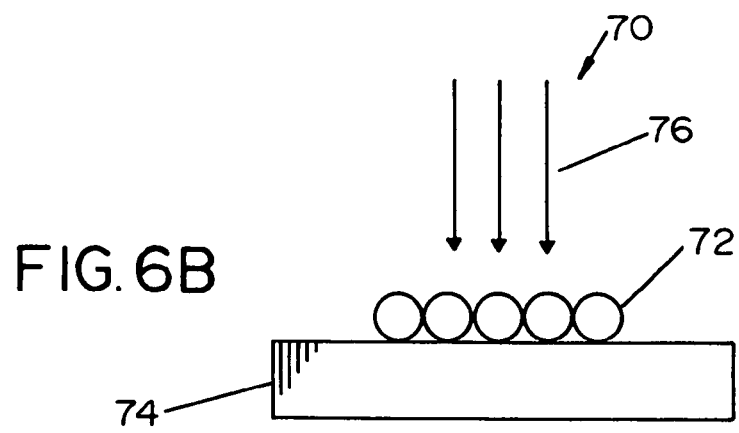

In order to overcome the shortcomings in detection of non-planar surfaces, a calibration technique is disclosed that can be used to calibrate multiple analytical devices for the analysis of regularly shaped (i.e., repeating) non-flat surfaces. In one embodiment, the non-flat surfaces may be a set of wires or rods placed in parallel to each other, and touching each other. Particularly, FIGS. 6A and 6B depict non-flat sample arrangement 70 having a sample 72 of regularly shaped non-flat surfaces located on a carrier 74. By use of the calibration technique to be described, these regularly shaped, non-flat surfaces may be analyzed by an analytical device that was only intended to analyze samples having flat surfaces. It is to be appreciated that while FIGS. 6A and 6B deal with rounded surfaces, the geometry to which the present application's concepts may be applied are not limited thereto. Rather, any regularly shaped non-flat surface can be analyzed using the calibration techniques described herein.

With more particular attention to FIG. 6A, the regularly shaped non-flat surface of sample 72 is shown with an X-ray fluorescence (XRF) spectroscopic analysis beam window 76 looking radially onto sample 72. FIG. 6B depicts sample 72 with the X-ray fluorescence (XRF) analysis beam window 76 looking radially onto sample 72. These figures illustrate that beam window 76 extends fully across to the edges of sample 72. It is to be appreciated that implementation of the following calibration technique will be benefited when calibration operations for different analytical devices provide a consistent location of the beam window from device to device.

Figure 4:
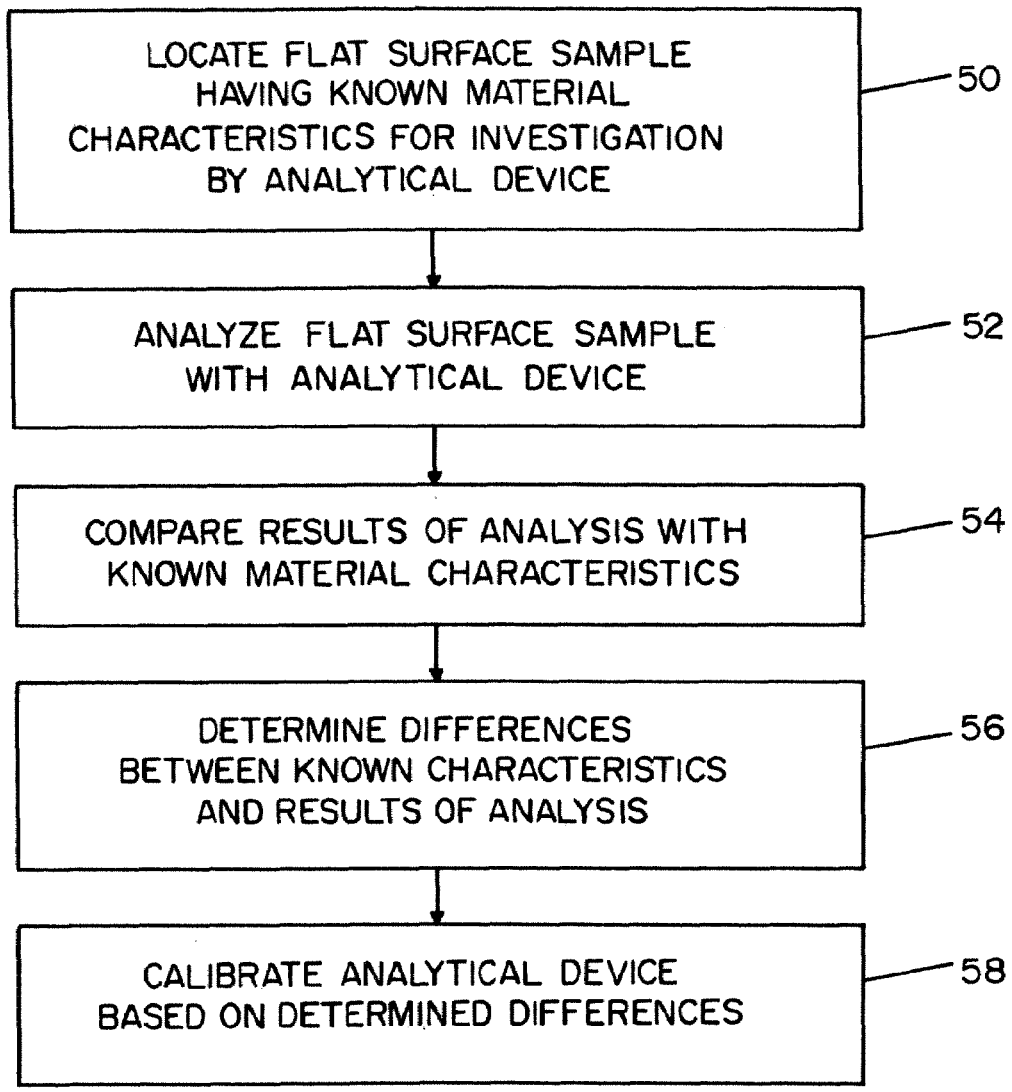
FIG. 4 is a flow chart for a know calibration process of a spectrometer using the flat sample or specimen such as shown in FIGS. 3A-3B.
Figure 7:
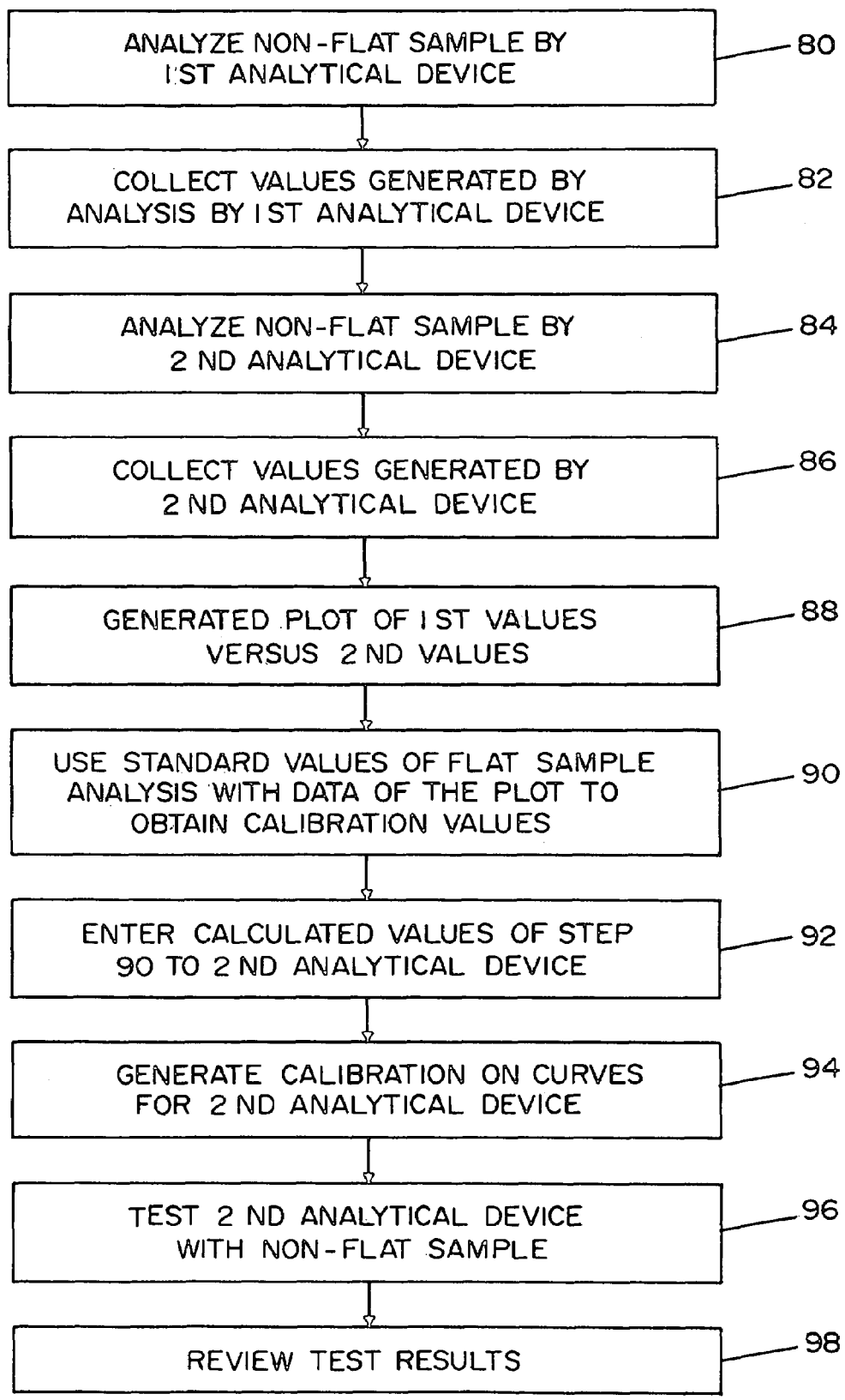
FIG. 7 is a flow chart for the calibration technique of the present application.

The flow diagram of FIG. 7 sets forth an embodiment of the calibration concepts according to the present application. In step 80, a non-flat sample is analyzed by a first analytical device, which has previously been calibrated for analysis of a flat surfaced sample. The flat surface calibration may have been obtained by the steps as shown in FIG. 4, or by other known flat surface calibration techniques, which generate flat surface calibration standard values.

The first analytical device may also be considered the "master device" to which other analytical devices are calibrated. Further, this master device may be calibrated for the non-flat sample surfaces in a manner similar to the process used for calibration of flat surface samples, as set out in FIG. 4. However, the following discussion teaches a manner to propagate calibration to other analytical devices, such that all the analytical devices calibrated in the following manner will provide similar results.

As shown in Table I, Sample materials A-E are determined to have particular values for detected elements (e.g., Element 1 Values and Element 2 Values).

TABLE I

| Standard Samples (flat sample) | Element 1 (E1) Values (flat sample) | Element 2 (E2) Values (flat sample) |
|---|---|---|
| Sample A | 0.35 | 0.10 |
| Sample B | 0.75 | 5.45 |
| Sample C | 1.25 | 2.85 |
| Sample D | 9.50 | 6.30 |
| Sample E | 15.75 | 11.50 |

Thus, a first analytical device has been calibrated for samples having flat surfaces. As mentioned in step 80, this calibrated first analytical device analyzes a non-flat sample such as shown in FIGS. 6A and 6B (it is to be appreciated multiple non-flat samples may be analyzed and the sample used may be selected to cover a range of elements and concentrations which are expected to be detected). Once this analysis has taken place, the values generated by this analysis are collected, as in step 82. Thereafter, in step 84, the same sample is provided to a second analytical device which has also been calibrated for flat samples in a manner similar to the first analytical device. The second analytical device (which is being calibrated for non-flat measurement) measures the non-flat sample. Values generated by the analysis of the non-flat sample, undertaken by the second analytical device, are then also collected, as in step 86. Using the values in collection steps 82 and 86, a plot of the values collected from operation of the first analytical device versus operation of the second analytical device is generated in step 88. The generated plot identifies point by point differences or deltas between generated values of the first analytical device and generated values of the second analytical device.

The relationship between the values generated by the analysis should be linear, and it is desirable to have an adjusted correlation coefficient of 90% or better.

The process by which the plot is generated may be by any number of statistical fitting techniques such as use of a linear regression algorithm which takes the standard linear form, $$y = mx + b$$

, where the values from the second analytical device (which is to be calibrated for non-flat samples) is plotted on the y-axis, values of the first analytical device (which may be considered the master analytical device) are plotted on the x-axis, m is the slope of line, and b is the intercept of the line. The plot is used in the procedure to obtain standard values for the non-calibrated second analytical, device.

In step 90, the process uses the standard values from the calibrated (for flat samples) first analytical device as shown in Table I, with the plotted results of the analysis collected in steps 82 and 86 of the second analysis device, to calculate final standard values for the second analytical device. More particularly, the calculation of these final standard values may be calculated in accordance with Table II.

TABLE II

| Sample (non-flat sample) | Element 1 Values (E1) (non-flat sample) | Element 2 Values (E2) (non-flat sample) |
|---|---|---|
| Sample A | $(0.35 - b_{E1}) \div m_{E1}$ | $(0.10 - b_{E2}) \div m_{E2}$ |
| Sample B | $(0.75 - b_{E1}) \div m_{E1}$ | $(5.45 - b_{E2}) \div m_{E2}$ |
| Sample C | $(1.25 - b_{E1}) \div m_{E1}$ | $(2.85 - b_{E2}) \div m_{E2}$ |
| Sample D | $(9.50 - b_{E1}) \div m_{E1}$ | $(6.30 - b_{E2}) \div m_{E2}$ |
| Sample E | $(15.75 - b_{E1}) \div m_{E1}$ | $(11.50 - b_{E2}) \div m_{E2}$ |

Next, in step 92, the calculated final standard values are entered as the standard values for generation of calibration curves for the second analytical device, and then in step 94 new calibration curves are generated for the second analytical device. Such calibration curve generation can be accomplished by known calibration programs including but not limited to SUPERQ, an XRF analysis software from PANalytical of 12 Michigan Drive, Natic, Mass., United States of America. The program is run by any appropriate computational system which is integrated into the analytical device or is a separate computing system which downloads the information to the analytical device.

With the new calibration curves incorporated into the second analytical device, the first and second analytical devices are tested, in step 96, to determine the degree of agreement using the same or other non-flat surface samples. The output will indicate the level of agreement between the two devices, which is then reviewed, in step 98, to determine whether or not there is sufficient similarity. If not, the process is repeated.

The preceding process or technique may also be repeated for investigation and calibration of different elements. It is to be appreciated the foregoing calibration technique can be implemented by any number of similar analytical devices. Also, the first analytical device which may be considered a master analytical device is the device from which other analytical devices are calibrated.

Thus, the standard values in Table I are useable in the generation of calibration curves for any number of similar analytical devices. Should the tabulated standard values not be available, and new standards are needed, the new standards should be developed on a drift-corrected, calibrated instrument and the new values used in place of the numerical constants in Tables I and II. The new set of standards can be prepared using samples having known element characteristics.

It is also to be understood that when locating the non-flat sample arrangement it is desired to have the analysis beam window (e.g., 76 of FIG. 6A) in the same location for the second analytical device as it was for the analysis by the first analytical device.

The process is useful for applications that are compatible with X-ray fluorescence (XRF) investigations of samples with regular, non-flat surfaces. The described techniques overcome the differences in each analytical device's geometry by transferring a calibration from a standard set of flat-plane samples to samples with a non-flat surface. In this way, each analytical devices' unique sample/detector interface can be calibrated to yield the same results for samples that do not have the typically-required flat surface at the point of measurement.

Figure 8:
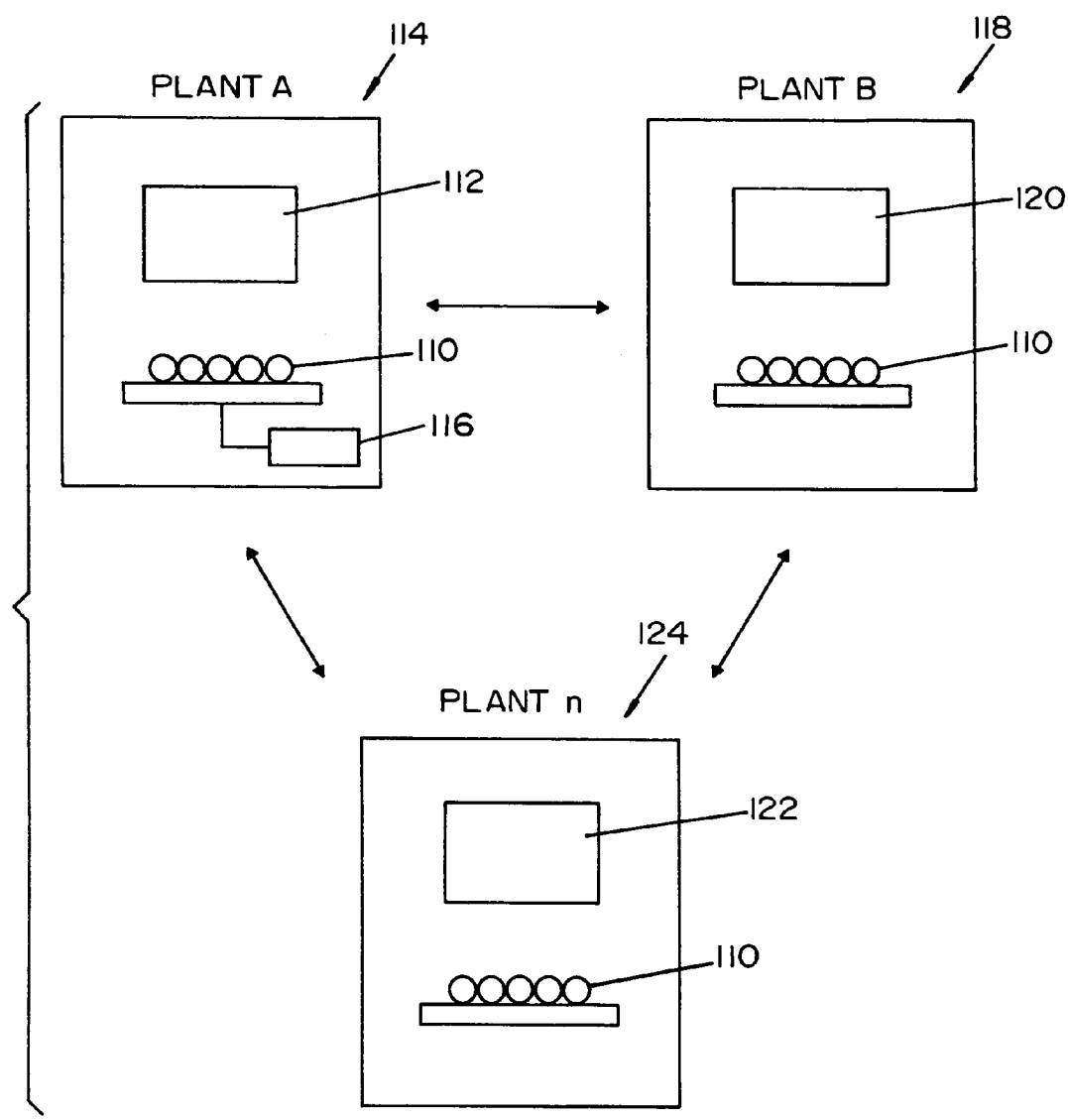
FIG. 8 illustrates calibration among a number of similar analytical devices.

Use of the above described system and technique finds particular application in the calibration of multiple analytical device of a similar type, such as X-ray fluorescence (XRF) spectrometers, found at separate locations. As depicted, in FIG. 8, for example, a series of tests are performed on welding wire samples 110 by XRF spectrometer 112 at Plant-A 114. In one instance such an investigation may show that an Element-X 116 has a favorable effect on welding properties when its XRF raw values lie between 5 and 10 as measured on XRF spectrometer 112. Although the wires presented a non-flat surface to the spectrometer, the relationship between the XRF readings and the wire performance is consistent, as the samples are all mounted as in FIGS. 5A and 5B.

Next, assuming the same welding wire needs to be manufactured at Plant-B 118, which also has an XRF spectrometer 120, but which is a different model (or it could even be the same model) from XRF spectrometer 112.

Using the present calibration technique and system, Plant-B 118 is able to calibrate its XRF spectrometer 120 to agree with the measurements taken at Plant-A 114. Subsequently, Plant-B 118 is able to manufacture welding wire with the same levels of Element-X 116 as Plant-A 114, even though Element-X was never actually quantified in terms of percent or any other normal concentration unit. This process can be repeated for other spectrometers within Plant-A or Plant-B, as well as those located in other plants, such as spectrometer 122 of Plant-n 124.

The above discussion illustrates a use of the present calibration concepts. Particularly, when the element being measured is not easily quantified, but can be shown to effect product performance, the present technique and system allows the user to forgo quantification and work with a relative unit of measure. This relative unit of measure can still be measured and controlled, even though the actual concentration of the element of interest is not known.

Thus, the described calibration technique and system does not require the user to know the actual concentration of the element of interest on the surface of the material, and it does not require the use of traditional flat geometry for the samples.

Although preferred embodiments have been depicted and described in detail herein, it is to be apparent to those skilled in the art that various modifications, additions, substitutions and the like can be made without departing from the spirit of the present embodiments and these are therefore considered to be within the scope of the present application as defined by the following claims.

The invention claimed is:

1. A method for calibrating an analytical device for analysis of non-flat surfaces comprising:
   analyzing a non-flat sample by a first analytical device previously calibrated for flat sample analysis wherein first analytical device flat sample standard values exist;
   collecting values generated by the analysis of the non-flat sample undertaken by the first analytical device;
   analyzing the non-flat sample by a second analytical device previously calibrated for flat sample analysis;
   collecting values generated by the analysis of the non-flat sample undertaken by the second analytical device;
   generating a plot of the values collected from the analysis of the non-flat sample by the first analytical device versus the values collected from the analysis of the non-flat sample by the second analytical device;
   calculating final standard values for the second analytical device using the standard values of the first analytical device and data of the generated plot to find a difference between the standard values of the first analytical device and the data of the generated plot; and
   generating calibration curves for the second analytical device using the calculated final standard values.

2. The method according to claim 1, further comprising:
   testing the first analytical device using the non-flat sample to obtain first analytical device test results;
   testing the second analytical device using the non-flat sample to obtain second analytical device test results; and
   comparing the first and second test results to determine a level of agreement between the first and second analytical devices.

3. The method according to claim 1, wherein the plot is generated by a statistical fitting process.

4. The method according to claim 1, wherein the plot is a linear regression plot.

5. The method according to claim 4, wherein a linear regression algorithm used to generate the linear regression plot takes a linear form of $$y = mx + b,$$

where y represents values of the first analytical device, x represents values of the second analytical device, m is a slope of the linear form, and b is the intercept of the linear form.

6. The method according to claim 1 wherein values generated by the second analytical device are relative units of measure and the relative units of measure of the second analytical device are relative units of measure, as to values of the first analytical device.

7. The method according to claim 1, wherein the generated plot identifies point-by-point differences between the values of the first analytical device and the values of the second analytical device.

8. The method according to claim 1, wherein the non-flat sample used with the first analytical device and the second analytical device is a same identical sample.

9. The method according to claim 1, further including positioning the non-flat sample in relation to the first analytical device and positioning the non-flat sample in relation to the second analytical device such that a beam window of the first analytical device and a beam window of the second analytical device impinge on substantially a same area of the non-flat sample.

10. The method according to claim 1, wherein the non-flat sample is a set of welding wire or rods placed parallel to and touching each other.

11. The method according to claim 1, wherein the calibration process transfers a calibration from a standard flat surface sample to a sample with a non-flat surface.

12. A system for calibrating an analytical device for analysis of non-flat surfaces comprising:
   a first analytical device calibrated for analysis of materials having a flat surface;
   standard values representing flat sample calibration values of the calibrated first analytical device;
   a second analytical device calibrated for analysis of materials having a flat surface;
   a non-flat sample having a non-flat repeating surface, wherein characteristics of the non-flat sample are known, and the non-flat sample is configured for analysis by the first analytical device and the second analytical device;
   a plot generating device arranged to receive output from the analysis of the non-flat sample by the first analytical device and the second analytical device and to generate a plot of the first analytical device analysis versus the second analytical device analysis;
   final standard values for the second analytical device calculated from the standard values of the first analytical device and data from the plot wherein the final standard values identify a difference between the standard values of the first analytical device and the data from the plot;

a calibration curve generator configured to receive the final standard values of the second analytical device and to generate calibration curves of the second analytical device.

13. The system according to claim 12, wherein the plot is a statistical fitted plot.

14. The system according to claim 12, wherein the plot is a linear regression plot.

15. The system according to claim 14, wherein the linear regression plot employs a linear form of $$y = mx + b,$$

where y represents values of the first analytical device, x represents values of the second analytical device, m is a slope of the linear form, and b is the intercept of the linear form.

16. The system according to claim 12 wherein values generated by the second analytical device are relative units of measure, and the relative units of measure of the second analytical device are relative units of measure, as to the values of the first analytical device.

17. The system according to claim 12, wherein the generated plot identifies point-by-point differences between the values of the first analytical device and the values of the second analytical device.

18. The system according to claim 12, wherein the non-flat sample used with the first analytical device and the second analytical device is a same identical sample.

19. The system according to claim 12, wherein the non-flat sample is a set of welding wire or rods placed parallel to and touching each other.

20. A method of calibrating an analytical device for analysis of non-flat surfaces comprising:

determining a master analytical device, wherein the master analytical device has associated master values used to calibrate a first analytical device;

comparing outputs of the master analytical device and a second analytical device, the compared outputs being generated from investigations of a master sample by each of the first and second analytical devices;

using the master values of the master analytical device and the compared outputs to identify differences between the master values and the compared outputs, to determine calibration values for the second analytical device for analysis of non-flat surfaces; and calibrating the second analytical device in accordance with the determined calibration values.

* * * * *